United States Patent [19]

Boys

[11] 3,982,419
[45] Sept. 28, 1976

[54] APPARATUS FOR AND METHOD OF DETERMINING ROTATIONAL AND LINEAR STIFFNESS

[75] Inventor: John T. Boys, Christ Church, New Zealand

[73] Assignee: Standard Pressed Steel Co., Jenkintown, Pa.

[22] Filed: Sept. 19, 1974

[21] Appl. No.: 507,417

Related U.S. Application Data

[63] Continuation-in-part of Ser. No. 357,920, May 7, 1973, abandoned.

[30] Foreign Application Priority Data

May 9, 1972 United Kingdom............... 21480/72

[52] U.S. Cl..................................... 73/139; 73/89; 173/12
[51] Int. Cl.[2]........................................ B25B 23/14
[58] Field of Search ................... 73/139, 99, 59, 89; 235/151.3; 81/52.5; 318/456, 488; 173/12

[56] References Cited
UNITED STATES PATENTS

| | | | |
|---|---|---|---|
| 2,912,861 | 11/1959 | Coyne et al...................... | 73/DIG. 1 |
| 3,558,866 | 1/1971 | Poulson ............................ | 73/89 X |
| 3,643,501 | 2/1972 | Pauley ............................... | 73/139 X |
| 3,661,012 | 5/1972 | Yamazaki et al....................... | 73/99 |
| 3,693,726 | 9/1972 | Hornig et al..................... | 73/139 X |
| 3,916,673 | 11/1975 | Gass et al. ............................... | 73/37 |

Primary Examiner—Charles A. Ruehl
Attorney, Agent, or Firm—Andrew L. Ney; Aaron Nerenberg; Robert P. Seitter

[57] ABSTRACT

A meter for determining stiffness or torque gradient including, in one embodiment, a deflectable coupling connected between an output shaft and a power input shaft, sensing means for developing two separate series of signals representative of the displacement of the input and output shafts respectively, a comparator for determining from the two series of signals a function of the stiffness or torque gradient and, in another embodiment, including a single shaft having an input end and an output end, transducer means associated with the shaft for developing a signal representative of the torque being applied through the shaft, sensing means for developing a signal representative of the displacement of the shaft, and comparator means for determining from the two signals a function of the stiffness or torque gradient. Either embodiment of the stiffness meter may be used for tightening a fastener by including an additional circuit responsive to the comparator output for sequentially storing information representative of the maximum stiffness developed up to any given point during the tightening operation and for producing a stop signal when the instantaneous stiffness has dropped to a predetermined ratio of the maximum stiffness.

89 Claims, 11 Drawing Figures

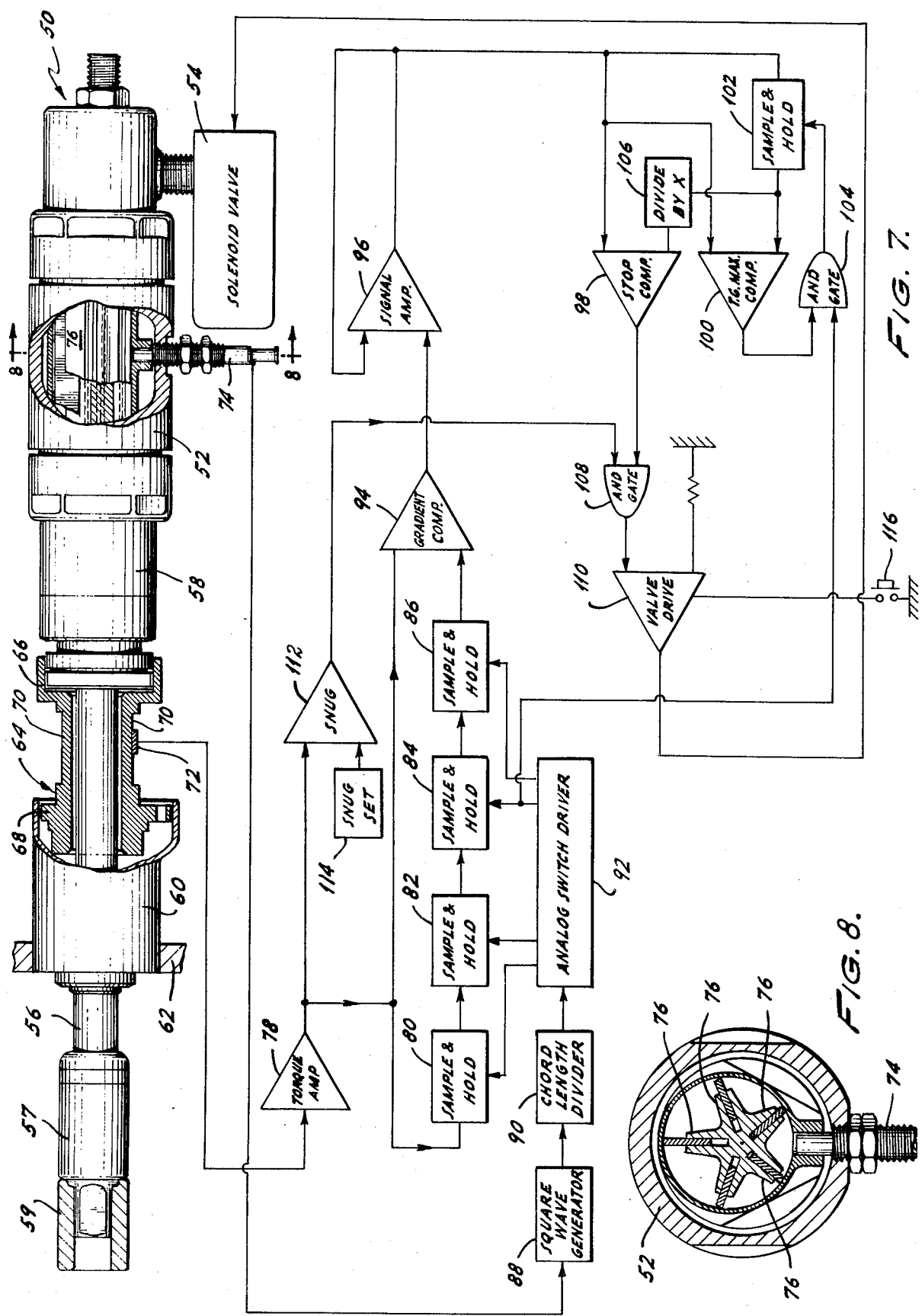

3,982,419

APPARATUS FOR AND METHOD OF DETERMINING ROTATIONAL AND LINEAR STIFFNESS

This application is a continuation-in-part of my copending application Ser. No. 357,920 filed May 7, 1973, now abandoned.

The invention relates to apparatus for and a method of determining rotational or linear stiffness and is particularly, but not exclusively, concerned with the tightening of screw-threaded or other axially-loaded fasteners.

The precise clamping load of a fastener is extremely important in determining whether or not a joint including the fastener will fail in service. It is therefore desirable that fasteners should be tightened to a consistent preload. An object of the present invention is to provide apparatus for and a method of tightening a screw-threaded fastener to a predetermined preload, for example, the maximum preload attainable without plastic deformation of the fastener or joint. Another object of the invention is to provide an improved stiffness meter or torque gradient meter not only for use in tightening fasteners but for other applications where stiffness or torque gradient is required to be determined.

The torque required to tighten a screw-threaded fastener is a function of several variables, namely the joint stiffness, the fastener stiffness, the surface friction and the thread form. The general characteristic showing the relationship between torque and angle of turning of a fastener is shown by the curve in FIG. 1 of the accompanying drawings, which shows torque plotted against angle of turning for a screw-threaded fastener in a typical application. The maximum gradient of the curve at a point A is a function of the variables set out hereinbefore. The gradient can vary widely even with a fastener of given diameter and thread configuration. The clamping load at which the gradient begins to fall below the maximum value has been found to be relatively independent of friction and joint stiffness and to be primarily dependent upon the yield strength of the fastener and/or the joint. The point indicated at X in FIG. 1 represents a point on the torque/angle of turning curve to which the fastener is tightened to a consistent tensile stress close to its yield stress. Further rotation of the fastener would cause the torque to approach a maximum value and the tensile stress in the fastener to approach its ultimate value. Depending on the ductility and dimensions of the fastener and/or the joint, fracture would finally occur at a point represented by Y.

The general objective in controlling the tightening of a screw-threaded fastener is to achieve a consistent joint preload close to the maximum that the fastener can apply without yielding commencing. One common method is to use a torque control by which a specific maximum torque is applied in an attempt to attain a desired preload for particular thread and frictional conditions. This method has the disadvantage that as the exact frictional conditions are not known under practical fastener assembly conditions, there will be variations in the torque/tension relationship. This leads to varying tensile loads in the fastener for a given applied torque. Another known method which is not dependent upon frictional conditions involves measuring the elongation of the fastener. In most cases direct measurement of elongation is impossible and therefore a modification of the method employs angle-controlled tightening in which an estimated elongation is effected by tightening to a precise angle of tightening. The disadvantage of this method is determining where to start measuring angles when operating on torque/angle of turning curves which have different initial and maximum slopes. For preloads in the elastic range this is extremely difficult as the deviation from a typical curve may be large. In the plastic range of the fastener, however, an error in angle does not change the preload appreciably and the deviation is small; but for very short fasteners this angle error may cause overstrain and consequent fracture. Angle controlled tightening is therefore only acceptable in the plastic region for long fasteners (for example those having more than six free threads) where some plastic deformation will not cause structural damage in the fastener.

It is therefore desirable that the optimum point at which tightening is to cease is the point where the gradient of the torque/angle of turning curve has just started to fall from its value in the generally linear region or its maximum value, that is the point at which the fastener is just beginning to yield. Taking X in FIG. 1 as a point where the gradient is a predetermined ratio of the gradient in the generally linear region or maximum achieved for the fastener, this point determines a practical position at which tightening should be stopped to give clamping loads which are essentially independent of the fastener geometry and the conditions of friction. A further object of the present invention is to provide a method and an apparatus for enabling the point X to be identified during a tightening operation as soon as it occurs so that the tightening process can be immediately stopped at that point and furthermore to enable the point to be identified independently of the joint or fastener characteristics, that is without foreknowledge of the joint or fastener characteristics or calibration.

According to the invention, apparatus for determining rotational or linear stiffness, i.e., a stiffness meter, comprises means for developing a changing signal representative of the instantaneous torque applied to a rotary member, storage means for storing a series of signals representative of instantaneous torque and gradient register means for sequentially comparing a stored signal with an instantaneous torque signal and developing a signal representative of the torque gradient.

The invention also provides a stiffness meter for determining the yield point or similarly significant change in slope of a torque-rotation curve, the meter comprising means for developing a signal representative of the gradient of the torque-rotation curve; means responsive to said gradient signal for storing an information signal representative of the gradient developed in the generally linear portion of the torque-rotation curve; and comparator means for comparing said gradient signal and said information signal and developing a control signal when said gradient has changed to a predetermined relationship with said information signal.

The stiffness meter may also include means for determining the largest gradient measured and the information signal is then representative of the largest gradient measured up to any point along the torque-rotation curve. Preferably, the control signal is developed when the gradient signal is about 50% of the information signal.

The invention also provides apparatus for tightening a fastener to the yield point or a similarly significant point including wrench means for applying torque and rotating the fastener; means for developing a signal representative of the instantaneous gradient of the torque-rotation curve through which the fastener is being tightened; and, means responsive to the gradient signal for determining the yield point or other similarly significant point on the torque-rotation curve through which the fastener is being tightened and for developing a control signal when the fastener is tightened to the determined point.

The fastener tightening apparatus determines the yield point or similarly significant point by storing an information signal representative of the gradient in the generally linear portion of the torque-rotation curve, preferably the largest gradient, and comparing the instantaneous gradient signal with the information signal and by developing the control signal when the compared signals have a predetermined relationship, preferably when the instantaneous gradient signal is 50% or less of the information signal.

According to certain embodiments of the invention, apparatus for determining rotational or linear stiffness, i.e., a stiffness meter, comprises output means for imparting movement to a member; input means for receiving power; deflectable coupling means between said output means and said input means for transmitting power from said input means to said output means; first sensing means responsive to said input means for developing a first series of signals representative of the displacement of said input means; second sensing means responsive to said output means for developing a second series of signals representative of the displacement by said coupling means of said output means, and comparator means responsive to said first and said second series of signals for determining the difference of the number of signals in said first and said second series of signals during a datum number of consecutive signals in said second series of signals as power is transmitted by said coupling means from said input means to said output means, said difference being a function of the stiffness.

The stiffness meter may also include circuit means responsive to said comparator means for sequentially storing information representative of the maximum stiffness or torque gradient developed up to any given point during the driving of said member.

The stiffness meter may be such as to be capable of being used as a wrench, torque input to said input means being stopped when said difference reaches a predetermined ratio of said maximum gradient stored by said circuit means.

Each of said first and second sensing means is conveniently an incremental encoder mounted on the respective input or output means and capable of emitting a precise number of equally-spaced signals during a complete rotation of the respective input or output means.

Certain embodiments of the invention also provide apparatus, for tightening a fastener, comprising fastener engaging means for imparting tightening movement to a fastener; power input means; deflectable coupling means between said fastener engaging means and said power input means for transmitting power to said fastener engaging means; first sensing means responsive to movement of said power input means for developing a first series of signals representative of the displacement of said power input means; second sensing means responsive to movement of said fastener engaging means for developing a second series of signals representative of the displacement by said coupling means of said fastener engaging means; comparator means responsive to said first and second signals for determining the difference of the number of signals in said first and second series of signals during a datum number of consecutive signals in said second series of signals as power is transmitted by said coupling means from said power input means to said fastener engaging means, said difference being a function of the instantaneous stiffness; circuit means responsive to said comparator means for sequentially storing information representative of the maximum stiffness developed during the tightening of the fastener and for producing a control signal when said instantaneous stiffness has dropped to a predetermined ratio of the maximum stiffness developed during the tightening of the fastener, and control means responsive to said control signal for controlling power input by said power input means.

Apparatus in accordance with certain embodiments of the invention may particularly, but not exclusively, be used for tightening a screw-threaded fastener, in which case the apparatus comprises fastener engaging means for imparting rotary movement to a threaded fastener; rotary power input means; torsionally deflectable coupling means between said fastener engaging means and said rotary power input means for transmitting rotary power to said fastener engaging means; first sensing means responsive to movement of said rotary power input means for developing a first series of signals representative of the rotary displacement of said rotary power input means; second sensing means responsive to said fastener engaging means for developing a second series of signals representative of the displacement by said coupling means of said fastener engaging means; comparator means responsive to said first and second signals for determining the difference of the number of signals in said first and second series of signals as rotary power is transmitted by said coupling means from said rotary power input means to said fastener engaging means, said difference being a function of the instantaneous torque gradient of the fastener; circuit means responsive to said comparator means for sequentially storing information representative of the maximum torque gradient developed during the tightening of the fastener and for producing a control signal when said instantaneous torque gradient has dropped to a predetermined ratio of the maximum torque gradient developed during the tightening of the fastener, and control means responsive to said control signal for controlling power input by said rotary power input means.

Certain embodiments of the invention may also provide a method of determining stiffness using deflectable coupling means for transmitting power from input means to output means for imparting movement to a member, the method consisting of the steps of developing a first series of signals representative of the displacement of said input means; developing a second series of signals representative of the displacement by said coupling means of said output means, and comparing said first and second series of signals by counting the difference of the number of signals in said first and second series of signals during a datum number of consecutive signals in said second series of signals as power is transmitted by said coupling means from said input means to said output means, said difference being a function of the stiffness of the member.

Certain embodiments of the invention may also provide a method of tightening a fastener by power input means driving fastener engaging means through deflectable coupling means, the method consisting of the steps of developing a first series of signals representative of the displacement of said power input means; a second series of signals representative of the displacement by said coupling means of said fastener engaging means; comparing said first and second series of signals by counting the difference of the number of signals in said first and second series of signals during a datum number of consecutive signals in said second series of signals as power is transmitted by said coupling means from said power input means to said fastener engaging means, said difference being a function of the instantaneous stiffness of the fastener; sequentially storing information representative of the maximum stiffness developed during the tightening of the fastener and producing a control signal controlling said power input means when said instantaneous stiffness has dropped to a predetermined ratio of the maximum stiffness developed during the tightening of the fastener.

Particularly, but not exclusively, the method according to certain embodiments of the invention may be for tightening a screw-threaded fastener by rotary power input means driving fastener engaging means through torsionally deflectable coupling means, the method consisting of the steps of developing a first series of signals representative of the rotary displacement of said rotary power input means; a second series of signals representative of the displacement by said coupling means of said fastener engaging means; comparing said first and second series of signals by counting the difference of the number of signals in said first and second series of signals during a datum number of consecutive signals in said second series of signals as power is transmitted by said coupling means from said rotary power input means to said fastener engaging means, said difference being a function of the instantaneous torque gradient of the fastener; sequentially storing information representative of the maximum torque gradient developed during the tightening of the fastener and producing a control signal controlling said rotary power input means when said instantaneous torque gradient has dropped to a predetermined ratio of the maximum torque gradient developed during the tightening of the fastener.

Desirably, the control signal may be produced when said instantaneous torque gradient has dropped to substantially 50% of the maximum torque gradient developed during the tightening of the fastener.

The control signal would usually be employed to stop the power input means; but in some applications it may be used to maintain the power input means to hold the instantaneous torque gradient at the aforesaid predetermined ratio of the maximum torque gradient.

The theory involved in the method and apparatus provided by the certain embodiments of the invention noted above is as follows:

Assuming that the coupling between the input and output means is or is equivalent to a torsionally-flexible shaft with a substantially linear characteristic having an incremental encoder mounted at each end thereof, if the torsional stiffness of the shaft is K and $\phi_1$ and $\phi_2$ are the angular displacements of the two ends of the shaft, the torque or turning moment M transmitted by the shaft $$= K (\phi_1 - \phi_2)$$

If the end of the shaft having the angular displacement $\phi_2$ is connected to the fastener to be tightened and the other end is attached to a motor or other driving means, the gradient of the torque/angle of turning characteristic being followed by the coupling, and therefore by the fastener, is given by:

$$\frac{dM}{d\phi_2} = K \left( \frac{d\phi_1}{d\phi_2} - 1 \right)$$

This equation may be evaluated in two alternative ways; the first of which is to expand the equation, as follows:

$$\frac{dM}{d\phi_2} = K \left( \frac{\frac{d\phi_1}{dt}}{\frac{d\phi_2}{dt}} - 1 \right)$$

$$= K \frac{\omega_1 - \omega_2}{\omega_2}$$

where $\omega_1$, $\omega_2$ are the angular velocities of the two ends of the shaft.

If the times between successive signals or pulses from the incremental shaft encoders are $t_1$ and $t_2$, then $$t_1 \alpha \frac{1}{\omega_1}, t_2 \alpha \frac{1}{\omega_2}$$

and thus, $$\frac{dM}{d\phi_2} = K \frac{t_2 - t_1}{t_1}$$

The times $t_1$ and $t_2$ can be measured electronically by means of the signals or pulses produced by the incremental encoders and after the necessary calculations by the gradient-determining means, an output signal proportional to $$\frac{dM}{d\phi_2}$$

can be obtained.

Alternatively, the equation $$\frac{dM}{d\phi_2} = K \left( \frac{d\phi_1}{d\phi_2} - 1 \right)$$

may be evaluated by employing small incremental values, as follows:

$$K \frac{\Delta\phi_1 - \Delta\phi_2}{\Delta\phi_2};$$

If high resolution incremental encoders giving of the order of four to five thousand pulses per revolution are employed, $\Delta\phi_2$ and $\Delta\phi_1$ are directly measurable by counting pulses. For example, if $\Delta\phi_2$ is determined by counting say 100 pulses by the encoder at the fastener end of the torque-transmitting coupling, the gradient is directly determined by counting the number of additional pulses produced by the encoder at the other end of the coupling during the production of the said 100 pulses by the encoder at the fastener end. If, for example, 6 extra pulses are counted at the encoder at the torque input end of the coupling, $$\frac{dM}{d\phi_2} \propto 6$$

Thus the gradient determining means either has to determine $$\frac{t_2 - t_1}{t_1}$$

be being responsive to the time intervals between pulses produced by the two encoders or it has to determine $$\frac{\Delta\phi_1 - \Delta\phi_2}{\Delta\phi_2}$$

merely by counting the numbers of pulses produced by the two encoders or by measuring the number of extra pulses produced by the encoder at the torque input end while the encoder at the fastener end produces a given number of pulses, e.g., 100.

According to certain other embodiments of the invention, a tightening apparatus is provided that includes a wrench for tightening a fastener, torque transducer means for developing a changing signal representative of the instantaneous torque being applied to the fastener and sensing means developing signals representative of fixed increments of rotation of the fastener. As in the certain embodiments discussed above, there is also provided shift register means receiving signals representative of instantaneous torque being applied to the fastener and which is clocked by signals from the sensing means for sequentially feeding signals to gradient register means, in the form of comparator means, subtracting torque signals outputted from the shift register means from the instantaneous signals outputted from the transducer means and for developing a signal representative of the instantaneous gradient of the torque-rotation curve which could be plotted for the particular fastener being tightened. Also as in the certain embodiments discussed above, the instantaneous gradient signal is compared with a gradient signal determined to be representative of the gradient of the torque-rotation curve in its generally linear portion and when the compared signals have a predetermined relationship, a control signal is developed.

The transducer means may be in the form of a torque cell associated with the wrench to measure the reaction torque on the wrench and the sensing means may include a proximity probe which is operatively mounted adjacent the rotary vanes of the motor input for the wrench for developing signals corresponding to the passage of the vanes and the rotation of the fastener.

Turning now, to FIG. 1 of the accompanying drawings, which is already stated is a typical Torque or Turning Moment versus Angle of Turning characteristic, the curve followed by the torque-transmitting coupling and hence by the fastener may be divided into three regions:-

I. An initial pre-tightening region;
II. A tightening region, and
III. A region of yield and subsequent failure of the fastener.

In region I the effect of burrs and irregularities in the threads of the fastener must be ignored and therefore the gradient-determining means of the torque-transmitting apparatus must first of all determine or be informed that region I has been left and the fastener is being tightened in region II. Conveniently entry into region II is by a torque measurement derived from the encoder signals. Normally the gradient of the characteristic will be substantially constant in region II, i.e., the curve will approximate to a straight-line; but if the characteristic is curved in region II it will reach a typical maximum value A. Acordingly, region II can be considered as the generally linear portion or region of the curve. When the fastener is tightened beyond region II, region III is reached, the gradient of the characteristic commences to decrease as the fastener begins to yield and ultimately the fastener would fail at point Y. The transition point X between regions II and III may be the point at which the gradient has been reduced by a certain proportion of the maximum gradient at A. It is desirable that a fastener should be tightened to point X and therefore the gradient-determining means must be capable of determining that region II has been reached and then of determining the instantaneous gradient during tightening and continuously comparing it with the gradient in region II, preferably, the maximum value A, to determine when the point X has been reached. The gradient-determining means may be any suitable logic circuit or circuits responsive to the signals received from the two encoders. When the gradient-determining means has detected that point X has been reached, it can issue a stop command so that the operator will stop the tightening of the fastener. Alternatively the stop command may be used to stop the driving motor or other means automatically.

Several forms of apparatus, for the tightening of a screw-threaded fastener, in accordance with the invention are now described with reference to the remainder of the accompanying drawings, in which.

Figure 6:
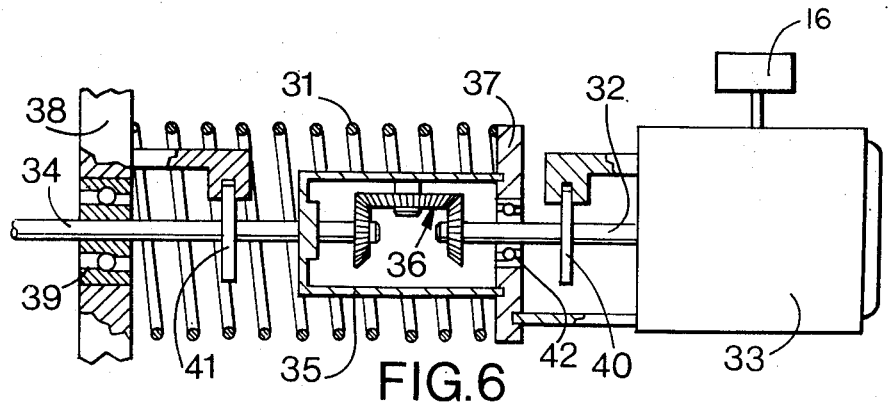

plotted against $\phi_2$;

FIG. 6 is an alternative form of the apparatus shown in elevation and part section;

FIG. 7 is another alternative form of the apparatus including the logic device; and FIG. 8 is a section view taken along the line 8—8 of FIG. 7.

Figure 2:
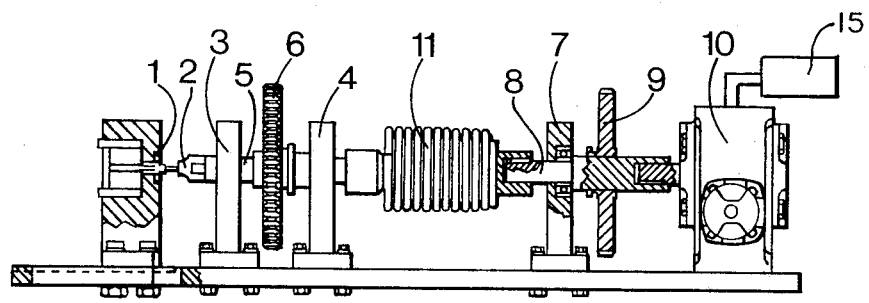
FIG. 2 is an elevation of the first form of the apparatus.

Referring to FIG. 2, a screw-threaded fastener is shown at 1, and this is engaged by a driver or other tool 2 for turning the fastener and having a shaft mounted for rotation in a bearing 3. The bearing 3 together with a companion bearing 4 supports a shaft 5 which is drivingly engaged with the tool 2 and carries a first incremental encoder 6. The apparatus also includes another bearing 7 supporting a shaft 8 carrying a second incremental encoder 9. The shaft 8 is arranged to be driven by a torque-applying motor 10 controlled by a suitable solenoid valve 15. The shafts 8 and 5 are interconnected by a helical spring 11. When the motor 10 is driven, it will rotate the shaft 8 and this in turn will rotate the helical spring 11 which will drive the shaft 5. The shaft 5 will turn the tool 2 which will tighten the fastener 1.

The encoders 6 and 9 may be of an optical, electromagnetic or other kind capable of producing signals in association with fixed light-responsive or other stationary receiver devices (not shown) which will produce a series of signals effected at precise intervals corresponding to the angular turning of the encoders or the angular velocities thereof and hence of the respective shafts 5 and 8. The frequency of the signals produced by the respective encoders 6 and 9 determines their respective angular velocities or a function thereof. The intervals between the signals produced by the encoders 6 and 9 can be measured, for example, by electronic means. From the time intervals between signals produced by the respective encoders or by counting the number of signals, as aforesaid, the gradient of the torque/angle of turning curve can be determined as explained herein and hence when the gradient has fallen to a value indicating that point X in FIG. 1 has been reached, the operator would stop the motor 10. The signals produced by the operation of the encoders 6 and 9 are fed into a logic device which produces a "stop" signal informing the operator that the motor 10 should be stopped, or the stop signal could be used to stop the motor automatically. Alternatively, instead of the signal produced by the logic device being a stop signal it may be used to hold the fastener under a substantially constant load, in which case the signal could be a controlling signal which prevents additional input power being supplied.

Figure 3:
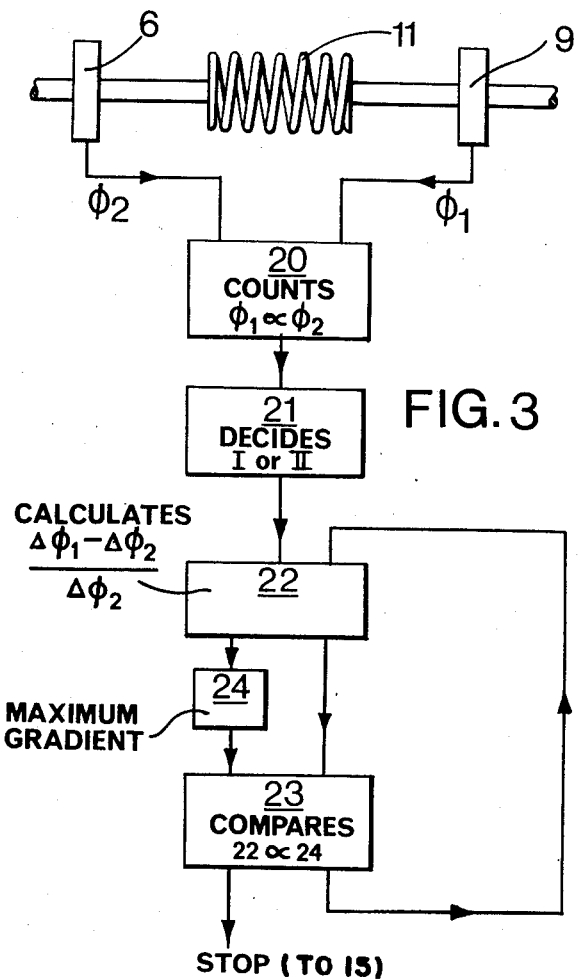
FIG. 3 is a diagram illustrating a logic device to be used in conjunction with the apparatus shown in FIG. 2.

Referring now to FIG. 3, the logic device is illustrated in block diagram form. Commencing at the top of the diagram, references 6 and 9 indicate the two encoders. The left-hand encoder, i.e., the one nearer to the fastener, issues pulses $\Phi_2$ and the right-hand encoder, i.e., the one nearer to the motor 10 issues pulses $\phi_1$. The two streams of pulses are supplied to a circuit illustrated by block 20. This counts the number of pulses $\phi_1$ and $\phi_2$ or determines the time intervals between the pulses of the respective streams of pulses or computes the gradient from measured angular velocities. A signal from block 20 passes to block 21 which is a logic circuit which decides whether region II has been reached. If the answer given by block 21 is affirmative, signals pass to block 22 which is a logic circuit which calculates the function of the gradient by determining $$\frac{\Delta\phi_1 - \Delta\phi_2}{\Delta\phi_2} \text{ or } \frac{t_2 - t_1}{t_1},$$

as aforesaid. Output signals from block 22 then pass to block 23. This is another logic circuit which compares the gradient function with a stored maximum function previously determined by block 22 and stored in a circuit indicated by block 24. Block 23 gives affirmative or negative output signals depending upon whether or not point X in FIG. 1 has been reached. If the output signal from block 23 is affirmative, this is the aforesaid stop command and tightening is immediately stopped, as aforesaid. If the output signal from block 23 is negative a signal is fed back to block 22 and the circuit thereof continues to continuously up-date the gradient function and feed an output signal to block 23.

Figure 4:
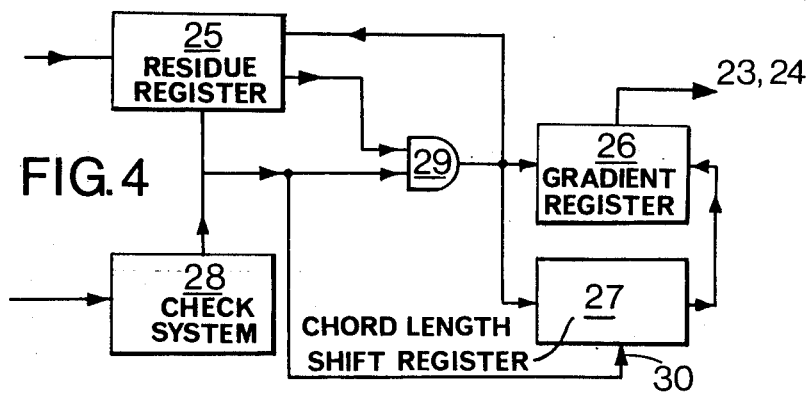
FIG. 4 is a particular part of the logic device of FIG. 2 shown in greater detail.

FIG. 4 is a schematic block diagram showing the main components of the electronic circuit indicated by the block 22 in FIG. 3. As already stated block 22 determines the gradient $$\frac{\Delta\phi_1 - \Delta\phi_2}{\Delta\phi_2} \text{ or } \frac{\Delta M}{\Delta\phi_2}.$$

The electronic circuit shown in FIG. 4 calculates the expression $$\frac{\Delta M}{\Delta\phi_2}$$

by measuring the number of $\phi_1$ pulses received from the input encoder 9 during a given value $\Delta\phi_2$. The value of $\Delta\phi_2$ chosen is referred to as the chord length because the measurement is equivalent to taking the difference between the readings of torque (M) across a chord of substantially constant length which is continuously moved along the M-$\phi$ curve as indicated by $a_1 b_1$ and $a_2 b_2$, in FIG. 1. The projection of the chord length on the $\phi$ axis is fixed by the characteristic or setting of a chord length shift register 27 which is operated each time it receives an actuating pulse, as hereinafter explained.

Pulses ($\phi_1$) received from the input encoder 9 at the motor end of the spring 11 are gated directly into a residue register 25 with due regard to the sense of rotation of the rotor. The function of the residue register 25 is to store $\phi_1$ pulses.

Figure 1:
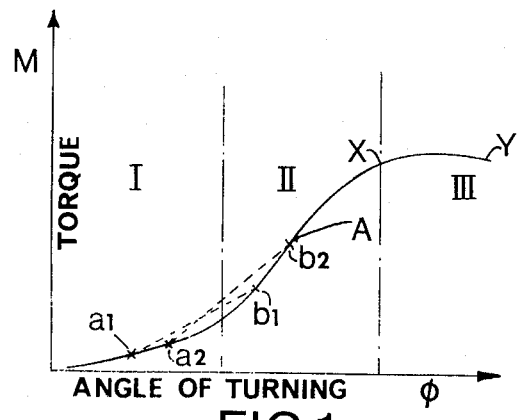
FIG. 1 is a typical curve of torque plotted against angle of turning experienced by a fastener during a tightening cycle and graphically illustrating an underlying principle of the invention.

Pulses ($\phi_2$) from the encoder 6 at the output or fastener end of the spring 11 are checked by a checking device 28 to determine whether the fastener is rotating in the correct direction and are then used to decrement the residue register 25. If the encoder 6 at the fastener end were to rotate backwards, the amount of backwards twist is counted and must be restored by an equal forward twist before any $\phi_2$ pulses are gated to the register 25. As soon as a $\phi_2$ pulse has decremented the residue register 25, the value shown thereby is examined. If it is greater than zero there have been more $\phi_1$ pulses than $\phi_2$ pulses and as a result a signal is passed through a gate 29 to both a gradient register 26 and the chord length shift register 27 and also to decrement the residue register 25. The chord length shift register 27 is actuated each time it receives a $\phi_2$ pulse passed by the checking device 28, as indicated by arrow 30, and if the shift register 27 also receives a pulse through the gate 29 it rgisters '1' at its input. If it does not receive a pulse through the gate 29 it registers '0', Each time the output of the shift register 27 register 1 it decrements the gradient register by one pulse. When the shift register output registers 0 it does not affect the gradient register. Thus each time the shift register is operated on by the production of a $\phi_2$ pulse in the correct sense, the gradient register either changes by one pulse or does not change depending upon whether there are positive "readings" by the residue register 25 and the output of the shift register 27. The chord length shift register 27 has a characteristic or a setting such that the gradient register reading is taken over the effective chord length. The chord length must be sufficiently long to average out the effect of "noise", that is unwanted signals superimposed on the basic signals. An angle of twist of 1° corresponding say to one $\phi_2$ pulse is too small for this purpose. It has been found that 20° is a suitable value of angle of twist over which to measure the torque; but if readings were only taken say every 20°, the Torque/Angle of Twist Curve could not be followed. Therefore the chords, such as $a_1 b_1$ and $a_2 b_2$ in FIG. 1 are overlapped and measurement of $$\frac{\Delta M}{\Delta \phi_2}$$

over a 20°chord are taken on each $\phi_2$ pulse that is about every 1° of twist. When the gradient register is operating normally, the indicated reading of the gradient register is $\Delta M/\Delta\phi_2$ for the fastener being tested. Signals from the gradient meter 26 are fed to the maximum gradient store, i.e., to block 24 and to the comparator in block 23 (see FIG. 3).

Figure 5:
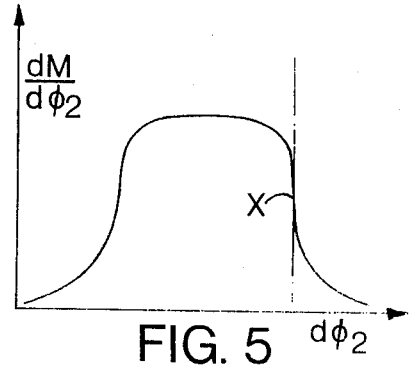
FIG. 5 is the derivative curve obtained from FIG. 1 that is the curve of $$\frac{dM}{d\phi_2}$$

The signal given by block 23 to stop the motor driving the fastener is produced when the instantaneous gradient has fallen to substantially 50° of the maximum gradient attained, that is, the gradient in the generally linear region of the M-$\phi_2$ curve. The reason for this is that the derivative of the M-$\phi_2$ curve, that is the $$\frac{dM}{d\phi_2} - \phi_2$$

curve shown in FIG. 5, has a point of inflexion at or near to the 50° of maximum value as indicated at X in FIG. 5. This point is also the steepest part of the curve and thus the point where the curve passes most quickly through a superimposed noise curve. Still referring to FIG. 5, it can be seen that point X lies within a range of about 25° to about 75° of the maximum value and a preset relationship utilizing a value within this range could be utilized to stop the motor driving the fastener. The point X is therefore the point on the curve which will give maximum immunity to noise, i.e., spurious signals.

Because the apparatus, in its fastener-tightening form, is essentially a torque gradient or torsional stiffness meter and it can compare the instantaneous torque gradient with the torque gradient in the generally linear region of the M-$\phi_2$ curve and, preferably with the maximum torque gradient, the limitations of existing systems for controlling the tightening of fasteners are overcome. These require relatively accurate pre-knowledge of the torque/angle characteristic, either by knowing the approximate value of the maximum gradient or by knowing the torque to provide a given clamping load or by knowing the angular rotation to ensure optimum clamping.

The apparatus described herein does not require pre-knowledge of a particular torque/angle of turning characteristic because the deviation of the instantaneous gradient from the gradient in the approximately linear region of the curve, preferably the maximum gradient, will be determined automatically and the tightening will be stopped automatically when the point X at which the instantaneous gradient is any preset fraction, e.g., substantially 50%, of the maximum gradient has been reached. It should also be clear that the instantaneous gradient may never exactly equal the preset fraction and, therefore, the apparatus should stop tightening when the instantaneous gradient is a preset fraction or less than the fraction of the maximum gradient. The invention, therefore, provides apparatus and a method preferable to known tightening systems.

Figure 2A:
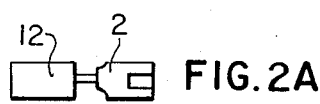
FIG. 2A is a partially schematic elevation view of a rotary-to-linear converter usable with the invention.

Using a technique analogous to that applied in the fastener-tightening form of the invention, the aforesaid torque gradient or torsional stiffness meter may be converted to a linear stiffness meter either by converting the output rotation into linear movement, for example with a rotary-to-linear converter 12 attached to the driver 2 as shown in FIG. 2A; such as a screw-thread or rack-and-pinion device. Alternatively linear encoders and a linear spring, or other linearly resilient element, connected between shaft means carrying the encoders may be employed. In this way, the point of yield in a linear system can be determined in a similar way to the determination of the point of yield in the aforesaid torsional system. Hence, for example, the yield point of tensile samples in a tension testing machine or a creep testing machine, can be identified without the measurement of gauge lengths and without the necessity to measure separately force and displacement.

Figure 2B:
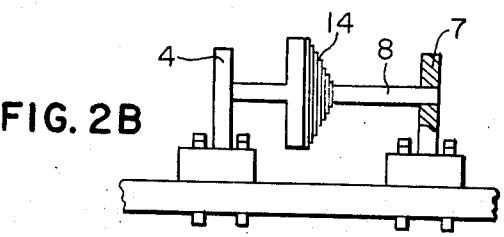
FIG. 2B is a partial elevation view of another embodiment of the invention using a spiral spring.
Figure 2C:
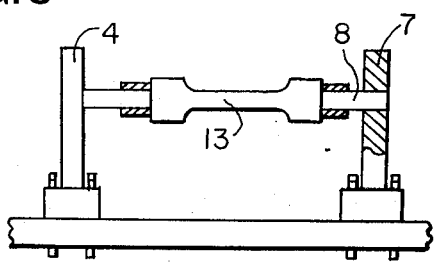
FIG. 2C is a partial elevation view of still another embodiment of the invention using a torsion bar.

Instead of using the helical spring 11 as the coupling means between the input and output shafts of a spiral spring 14 may be employed as shown in FIG. 2B. Alternatively, the torque transmitting coupling may be a torsion bar or tube 13 as shown in FIG. 2C and connected between the input and output shaft means or having end portions forming said input and output shaft means. The torsion bar or tube may be of metal, rubber, plastics or it may be a composite bar or tube formed from any of these materials.

FIG. 6 shows an alternative form of the apparatus which can be used instead of that shown in FIG. 2. In FIG. 2, the spring 11 is rotated about its longitudinal axis in addition to being twised as the fastener follows the Torque/Angle of Turning Curve shown in FIG. 1. In some instances this may be undesirable and instead the apparatus shown in FIG. 6 could be employed in which a non-rotatable helical spring 31 transmits torque between an input shaft 32 driven by a motor 33 controlled by a suitable solenoid valve 16 to an output shaft 34 by which a fastener or other member to be turned is arranged to be driven. The input shaft 32 is connected through a gear box 35 containing a gear drive, shown for diagrammatic purposes as a simple differential gear train 36, to the output shaft 34. When the input shaft 32 is driving the output shaft 34 at the same speed, i.e., when the torque M is constant, there will be no bodily movement of the gear train 36; but when the input shaft starts to move faster than the output shaft, that is as in region II in FIG. 1, the gear train will swing about the common axis of the shafts 32 and 34 and transmit the swinging movement to the housing of the gear box 35. One end of the spring 31 is attached to an end wall 37 of the gear box 35 which is mounted for swinging about the common axis of the shafts 32 and 34 on a bearing 42. The other end of the spring is attached to a fixed mounting plate 38 in which the output shaft 34 is freely rotatable in a bearing 39. The input shaft 32 carries an incremental encoder 40, equivalent to the encoder 9 in FIG. 2, and the output shaft 34 carries an incremental encoder 41, equivalent to the encoder 6 in FIG. 2. When the point X is approached and there is a change in the rate of differential rotation between the input and output shafts, the spring 31 will transmit torque in a similar manner to the spring 11 in FIG. 2; but the spring 31 does not rotate, it only twists and therefore does not have to be dynamically balanced. The angular deviation between the shafts will be measured by the encoders 40 and 41 and their signals will be transmitted through and handled by the logic devices shown in FIGS. 3 and 4 in the way already described. Another advantage of the arrangement shown in FIG. 6 is that the axial length of the apparatus can be reduced because the gear box 35 can be made short and housed within the spring 31 as shown. Also the encoders may be positioned within the spring. Alternatively, the encoder 40 can be positioned at the input end of the gear box, as shown, and so a low resolution encoder can be used, thereby saving cost.

In either arrangement (i. e., FIG. 2 or FIG. 6) of the apparatus, the logic devices may include switch means to enable the apparatus to be used as a normal tightening device or wrench in which the torque is transmitted from the motor to the fastener without indication of deviation from a linear Torque/Angle of Turning relationship and without automatic stopping of the driving motor.

Although in FIG. 2, a helical spring 11 has been used as the coupling means between the input and output shafts, that is the apparatus is employed as a wrench to which input torque is applied continuously during tightening, the apparatus could be used as an impact wrench, that is a wrench of the kind to which input torque is applied intermittently in steps, by using in place of the spring 11 a coupling means which has a non-resilient, substantially linear M-$\phi$ characteristic. The coupling means would in such a case be effectively a non-return type of spring to prevent recoil of the appartus between the periods during which input torque is applied.

Another embodiment of the apparatus is illustrated in FIGS. 7 and 8 and includes certain means reducing the cost of the apparatus relative to the embodiment shown in FIGS. 2–4. As shown in FIG. 7, the apparatus comprises a wrench 50 including an air motor 52, the operation of which is controlled by a suitable solenoid valve 54, and which drives an output shaft 56 through a speed-reducing gear box 58 so that the output shaft does not rotate at the same high speed as the motor. Output shaft 56 carries an adapter 57 for attachment with a driver bit 59 and is mounted in a suitable rotary bearing assembly 60 facilitating rotation of and taking up any bending stresses in the output shaft. Bearing assembly 60 may be mounted on a rigid frame 62, but use of the frame is not necessary for the practice of the invention. At this point it should be noted that while motor 52 has been described as an air motor, it may be of any suitable type, for example electric, hydraulic or any combination of pneumatic electric or hydraulic. It should also be noted that the apparatus thus far described is generally conventional and need not be explained in greater detail.

Located between gear box 58 and bearing assembly 60 is transducer means in the form of a torque cell 64 which develops a signal representative of the instantaneous torque being applied to the fastener. Torque cell 64 includes a first mounting base 66 securing the cell to gear box 58 and a second mounting base 68 securing it to bearing assembly 60. Extending axially of the wrench between mounting bases 66 and 68 are a plurality of strut members 70 which are somewhat deformable, that is, are relatively rigid members capable of twisting somewhat about the axis of the wrench. When wrench 50 is operative to tighten a fastener, the reaction torque action thereon causes strut member 70 to twist about the axis of the wrench, the amount of twist being proportional to the reaction torque which of course, is equal to and opposite the torque being applied to the fastener. Each strut member 70 carries a strain gauge 72 which is connected in a wheatstone bridge circuit (not shown) to develop an electric signal representative of the instantaneous torque being applied to the fastener. Instead of strain gauges, contacting or proximity displacement gauges could be used to develop the electric signal. Thus, with the torque cell arrangement disclosed in this embodiment, one of the encoders and the spring arrangement disclosed in the apparatus illustrated in FIGS. 2–4 have been replaced by a relatively inexpensive transducer. The exact form of torque cell 64, of course, may vary somewhat. For example, struts 70 could be replaced by a somewhat deformable cylindrical member, if desired.

Since one encoder in FIGS. 2–4 embodiment of the invention has been replaced by torque cell 64, it should be clear that only one encoder need be utilized. However, in accordance with this embodiment of the invention, it can be replaced by a relatively inexpensive sensing means further reducing the cost of the apparatus. Accordingly, further disclosed in this embodiment of the apparatus is a proximity probe 74 mounted through the housing of motor 52 adjacent to and radially spaced from rotary vanes 76 in the motor, as illustrated most clearly in FIG. 8. Proximity probe 74 can be in the form of an induction coil which develops an electrical signal when metal passes through its magnetic field. Thus, as vanes 76 rotate when the fastener is being tightened, signals are provided by proximity probe 74 which represent fixed increments of rotation of the fastener. The size of the increments depends on the number of vanes 76 in motor 52 and the gear ratio of gear box 58. It should be understood of course, that proximity probe could cooperate with one of the gears in gear box 58 in a similar manner.

Still referring to FIG. 7, a control system functionally equivalent to that illustrated in FIGS. 3 and 4 of the drawing is illustrated and further reduces the cost of the system by utilizing certain analog circuitry. The output signal from torque cell 64 representative of the instantaneous torque being applied to the fastener is fed through a torque amplifier 78 which amplifies the torque signal to a magnitude wherein it is compatible with the rest of the control system. From amplifier 78, the torque signal is fed through shift register means which, since the circuit is analog, comprises a series of charge coupled devices in the form of sample and hold circuits 80, 82, 84 and 86. As in the circuits illustrated in FIGS. 3 and 4, the gradient shift register means is clocked by signals representative of fixed angular increments of displacement of the fastener. Accordingly, signals from proximity probe 74 which are in the form of spike shaped pulses are fed through a square wave generator 88 which shapes the signals and feeds the shaped signals through a chord length divider 90 to an analog switch driver 92 which sequentially clocks the sample and hold circuits. Chord length divider 90 is a suitable divider circuit which electronically divides the pulses from square wave generator 88 by 1, 2, 4, 8, 16 or 32 so that every pulse, or every second pulse, or every fourth pulse, etc., is utilized to clock the shift register. By selecting the appropriate division to be made in chord length divider 90, it is possible to adjust the chord length on the Torque-Angle of Turning curve over which the torque gradient is measured, that is, chord length a-b in FIG. 1.

Analog switch driver 92, although not necessary, assures that each sample and hold circuit has discharged its stored signal before receiving a new signal. Accordingly, analog switch driver 92 sequentially clocks the sample and hold circuits first clocking circuit 86, then circuit 84, then circuit 82, and finally circuit 80. Accordingly, sample and hold circuit 86 has discharged its stored signal prior to receiving a new signal from sample and hold circuit 84, etc. The output from sample and hold circuit 86 is representative of torque a fixed increment of rotation prior to that particular instant and is fed through a gradient register or comparator circuit 94 in the form of a differential amplifier which also receives an input signal representative of the instantaneous torque being applied to the fastener from torque amplifier 78. As in the circuits illustrated in FIGS. 3 and 4, comparator 94 subtracts its input signals and has an output signal representative of the instantaneous torque gradient for the particular fastener being tightened. The gradient signal from comparator 94 is fed through a suitable gradient amplifer 96 which amplifies it to a magnitude compatible with the rest of the control system.

From gradient signal amplifier 96, the instantaneous gradient signal is fed to means for determining the maximum gradient and also to means for comparing the maximum and instantaneous gradient signals. Looking first at the means for determining the maximum gradient, there is included a maximum gradient comparator 100 receiving input signals from gradient signal amplifier 96 and from a sample and hold circuit 102 which also receives signals from gradient signal amplifier 96. As will be made clear hereinafter, sample and hold circuit 102 stores a signal representative of the maximum gradient encountered up to any point in the tightening cycle prior to the instantaneous output from the gradient signal amplifier. Comparator 100 determines whether the instantaneous gradient signal from gradient signal amplifier 96 or the previously stored signal from sample and hold circuit 102 is larger. If the instantaneous gradient signal is larger, comparator 100 feeds an output signal to an AND gate 104 which also receives signals from analog switch driver 92 when the switch driver outputs a clocking signal to sample and hold circuit 84. When both signals are received by AND gate 104, it outputs a clocking signal to sample and hold circuit 102 which allows the sample and hold circuit to receive a new signal from gradient signal amplifier 96 representative of the larger gradient. If the instaneous gradient is smaller, comparator 100 provides no output, nor does AND gate 104 so that sample and hold circuit 102 cannot accept a new gradient signal. By utilizing the clocking signal from analog switch driver 92 to sample and hold circuit 84, a time lag is provided which allows the comparison to be made before a clocking signal can be fed through AND gate 104 and before a new gradient signal can be developed.

Looking now at the means for comparing the maximum and instantaneous gradient signals, it can be seen that as the signal representative of the maximum gradient is fed from sample and hold circuit 102 to comparator 100 it is split and fed to a division circuit 106 which is operative to divide the signal by the preset relationship utilized to determine the point X on the curve illustrated in FIG. 1 or FIG. 2. If the preset relationship is 50%, as is preferred as noted above, dividing circuit 106 splits the maximum stored gradient signal in half and feeds the signal to a control comparator 98 so that it may be compared with an instantaneous gradient signal from gradient signal amplifier 96 which is also fed to the control comparator. When the input signals to control comparator 98 are equal, or when the gradient signal is smaller than the divided maximum gradient signal, the control comparator provides an output signal which is fed to another AND gate 108. At this point, it should be noted that the output signal from comparator 98 could be fed directly through a valve drive amplifier 110 which would amplify the signal to a suitable magnitude to close the solenoid in valve 54 and stop motor 52. However, to assure that comparator 98 does not inadvertently provide an output signal in Region 1 of the curve illustrated in FIG. 1, AND gate 108 is utilized and receives an additional input signal from a snug torque comparator 112. Instantaneous torque signals are fed from torque amplifier 78 to snug torque comparator 112 which also receives an input signal from a preset snug torque signal generator 114 which, of course, could be in the form of a suitable potentiometer for providing a predetermined input signal representative of the torque approximately corresponding to that at the point marking the transition from Region 1 to Region 2 on the curve illustrated in FIG. 1. The noted point is commonly referred to as the snug point or snug torque point. The setting in snug torque signal generator 114 need not be exactly representative of the snug point and may be an approximation, for example, a signal representative of about 20% of the torque valve expected at the yield point would suffice. When the instantaneous torque signal from amplifier 78 exceeds that generated by snug torque signal generator 114, comparator 112 provides an output signal to AND gate 108 which allows the feeding of the signal from control comparator 98 to valve drive amplifier 110. The output of valve drive amplifier 110 is fed to control valve 54, closing same and stopping motor 52. Thus, any signals inadvertently developed by control comparator 98 in the pretightening region, that is Region 1, of the curve illustrated in FIG. 1 would not close control valve 54.

Finally, a reset switch 116 is provided which can be utilized to clear the circuits and prepare the tool for a new tightening operation with another fastener. One other point that should be noted involves the fact that the various predetermined relationships can be utilized to determine when to stop the tightening cycle depending on the characteristic of the torque rotation curve. For example, if the curve included a temporary flattening at a known load less than the load at the yield point, the tool could be utilized to stop tightening at that point. Such a temporary flattening of the curve could be caused by a particular fastener configuration.

In the foregoing, there has been disclosed several embodiments of the invention and it should be obvious to one skilled in the art that various modifications and changes can be made without departing from the true spirit and scope of the invention as recited in the appended claims.

I claim:

1. A meter for determining the stiffness of an assembly including a member comprising:
   output means for imparting movement to the member;
   input means for receiving power;
   deflectable coupling means between said output means and said input means for transmitting power from said input means to said output means;
   first sensing means responsive to said input means for developing a first series of signals representative of the displacement of said input means;
   second sensing means responsive to said output means for developing a second series of signals representative of the displacement by said coupling means of said output means, and
   comparator means responsive to said first and said second series of signals for determining the difference of the number of signals in said first and said second series of signals during a datum number of consecutive signals in said second series of signals as power is transmitted by said coupling means from said input means to said output means, said difference being a function of the stiffness of said assembly.

2. A meter according to claim 1 including circuit means responsive to said comparator means for sequentially storing information representative of the maximum stiffness developed up to any given point during the driving of said member.

3. A meter according to claim 1 in which said coupling means is substantially linearly resilient.

4. A meter according to claim 1 in which said coupling means has a non-resilient substantially linear torque/angle of turning characteristic.

5. A meter for determining the stiffness of an assembly including a member comprising:
   output means for imparting movement to the member;
   input means for receiving power;
   deflectable coupling means between said output means and said input means for transmitting power from said input means to said output means;
   first sensing means responsive to said input means for developing a first series of pulses representative of the displacement of said input means;
   second sensing means responsive to said output means for developing a second series of pulses representative of the displacement by said coupling means of said output means, and
   comparator means responsive to said first and said second series of pulses for determining the difference of the number of pulses in said first and said second series of pulses during a datum number of consecutive pulses in said second series of pulses as power is transmitted by said coupling means for said input means to said output means, said difference being a function of the stiffness of said assembly.

6. A meter according to claim 5 in which said comparator means includes control means responsive to selected pulses of said second series and counting means for counting said datum number of said second series of pulses, said control means being capable of activating said counting means to initiate a count of said datum number of pulses for each of said selected pulses.

7. A meter according to claim 6 in which each pulse in said second series is a selected pulse, whereby said counting means is activated to initiate a count of said datum number of pulses for each pulse in said second series.

8. A meter for determining torque gradient of an assembly including a member comprising:
   output means for imparting rotary movement to the member;
   input means for receiving rotary power;
   torsionally deflectable coupling means between said output means and said input means for transmitting torque from said input means to said output means;
   first sensing means responsive to said input means for developing a first series of signals representative of the rotary displacement of said input means;
   second sensing means responsive to said output means for developing a second series of signals representative of the rotary displacement by said coupling means of said output means, and
   comparator means responsive to said first and second series of signals for determining the difference of the number of signals in said first and said second series of signals during a datum number of consecutive signals in said second series of signals as power is transmitted by said coupling means from said input means to said output means, said difference being a function of the gradient of the torque operatively transmitted by said coupling means to the member.

9. A meter according to claim 8 including circuit means responsive to said comparator means for sequentially storing information representative of the maximum torque gradient developed up to any given point during the driving of said member.

10. A meter according to claim 4 wherein said output means imparts linear motion to said assembly by a rotary-to-linear converter, and wherein said torque gradient is indicative of the linear torque gradient of said assembly.

11. A meter according to claim 8 in which the coupling means is a helical spring.

12. A meter according to claim 8 in which the coupling means is a spiral spring.

13. A meter according to claim 8 in which the coupling means is a torsion bar.

14. A meter according to claim 8 in which each of said first and second sensing means is an incremental encoder mounted on the respective input and output means and capable of emitting a precise number of equally-spaced pulses during a complete rotation of the respective input and output means.

15. A meter for determining torque gradient of an assembly including a member comprising:
   output means for imparting rotary movement to the member;
   input means for receiving rotary power;
   torsionally deflectable coupling means between said output means and said input means for transmitting torque from said input means to said output means;
   first sensing means responsive to said input means for developing a first series of pulses representative of the rotary displacement of said input means;
   second sensing means responsive to said output means for developing a second series of pulses representative of the rotary displacement by said coupling means of said output means;

comparator means responsive to said first and second series of pulses for determining the difference of the number of pulses in said first and said second series of pulses during a datum number of consecutive pulses in said second series of pulses as power is transmitted by said coupling means from said input means to said output means, said difference being a function of the gradient of the torque transmitted by the coupling means, and circuit means responsive to said comparator means for sequentially storing information representative of the maximum torque gradient developed up to any given point during the driving of said member.

16. A meter according to claim 15 capable of being used as a wrench, torque input to said input means being stopped when said difference reaches a predetermined ratio of said maximum torque gradient stored by said circuit means.

17. A meter according to claim 16 capable of being used as a wrench of the impact kind in which torque input is applied intermittently in steps, said coupling means having a non-resilient, substantially linear torque/angle of turning characteristic.

18. Apparatus for tightening an assembly including a fastener comprising:

fastener engaging means for imparting tightening movement to the fastener;

power input means;

deflectable coupling means between said fastener engaging means and said power input means for transmitting power to said fastener engaging means;

first sensing means responsive to movement of said power input means for developing a first series of signals representative of the displacement of said power input means;

second sensing means responsive to movement of said fastener engaging means for developing a second series of signals representative of the displacement by said coupling means of said fastener engaging means;

comparator means responsive to signals of said first and second series for determining the difference of the number of signals in said first and second series of signals during a datum number of consecutive signals in said second series of signals as power is transmitted by said coupling means from said power input means to said fastener engaging means, said difference being a function of the instantaneous stiffness of the assembly;

circuit means responsive to said comparator means for sequentially storing information representative of the maximum stiffness of the assembly developed during the tightening of the assembly and for producing a control signal when said instantaneous stiffness has dropped to a predetermined ratio of the maximum stiffness developed during the tightening of the assembly and control means responsive to said control signal for controlling power input by said power input means.

19. Apparatus for tightening an assembly including a fastener comprising:

fastener engaging means for imparting tightening movement to the fastener;

power input means;

deflectable coupling means between said fastener engaging means and said power input means for transmitting power to said fastener engaging means;

first sensing means responsive to movement of said power input means for developing a first series of pulses representative of the displacement of said power input means;

second sensing means responsive to movement of said fastener engaging means for developing a second series of pulses representative of the displacement by said coupling means of said fastener engaging means;

comparator means responsive to pulses by said first and second series for determining the difference of the number of pulses in said first and second series of pulses during a datum number of consecutive pulses in said second series of pulses as power is transmitted by said coupling means from said power input means to said fastener engaging means, said difference being a function of the instantaneous stiffness of the assembly;

circuit means responsive to said comparator means for sequentially storing information representative of the maximum stiffness of the assembly developed during the tightening of the assembly and for producing a control signal when said instantaneous stiffness has dropped to a predetermined ratio of the maximum stiffness developed during the tightening of the assembly, and control means responsive to said control signal for controlling power input by said power input means.

20. Apparatus for tightening a screw-threaded fastener comprising:

fastener engaging means for imparting rotary movement to a threaded fastener;

rotary power input means;

torsionally deflectable coupling means between said fastener engaging means and said rotary power input means for transmitting rotary power to said fastener engaging means;

first sensing means responsive to movement of said rotary power input means for developing a first series of signals representative of the rotary displacement of said rotary power input means;

second sensing means responsive to said fastener engaging means for developing a second series of signals representative of the displacement by said coupling means of said fastener engaging means;

comparator means responsive to signals of said first and second series for determining the difference of the number of signals in said first and second series of signals as rotary power is transmitted by said coupling means from said rotary power input means to said fastener engaging means, said difference being a function of the instantaneous torque gradient of the fastener;

circuit means responsive to said comparator means for sequentially storing information representative of the maximum torque gradient developed during the tightening of the fastener and for producing a control signal when said instantaneous torque gradient has dropped to a predetermined ratio of the maximum torque gradient developed during the tightening of the fastener, and control means responsive to said control signal for controlling power input by said rotary power input means.

21. Apparatus according to claim 20 in which one end of said torsionally deflectable coupling means is directly connected to said rotary power input means and the other end of said torsionally deflectable coupling means is directly connected to said fastener engaging means.

22. Apparatus according to claim 21 in which said torsionally deflectable coupling means is flexible and has an elastic characteristic.

23. Apparatus according to claim 22 in which said torsionally deflectable coupling means is a helical spring.

24. Apparatus according to claim 20 including a transmission permitting relative rotational movement between said rotary power input means and said fastener engaging means, fixed structure supporting one end of said torsionally deflectable coupling means and said rotary power input means, the other end of said torsionally deflectable coupling means being movable in response to rotary movement of said fastener engaging means relative to said rotary power input means.

25. Apparatus according to claim 24 in which said torsionally deflectable coupling means is flexible and has an elastic characteristic.

26. Apparatus according to claim 25 in which said torsionally deflectable coupling means is a helical spring.

27. Apparatus as claimed in claim 20 capable of being used as a wrench of the impact kind in which torque is applied to said input means intermittently in steps, said torsionally deflectable coupling means having a non-resilient, substantially linear torque/angle of turning characteristic.

28. Apparatus according to claim 20 in which said control signal is produced when said instantaneous torque gradient has dropped to substantially 50% of the maximum torque gradient developed during the tightening of the fastener.

29. Apparatus as claimed in claim 20 in which said control means is arranged to stop power input by said power input means on receipt of said control signal.

30. The method of determining stiffness if on assembly using deflectable coupling means for transmitting power from input means to output means for imparting movement to the assembly, the method consisting of the steps of developing a first series of signals representative of the displacement of said input means;
developing a second series of signals representative of the displacement by said coupling means of said output means, and
comparing said first and second series of signals by counting the difference of the number of signals in said first and second series of signals during a datum number of consecutive signals in said second series of signals as power is transmitted by said coupling means from said input means to said output means, said difference being a function of the stiffness of said assembly.

31. The method according to claim 30 wherein said output means imparts rotary movement to said assembly; said input means receives rotary power; said coupling means is capable of transmitting torque from said input means to said output means, and said first and second series of signals are representative of the rotary displacement of said input means and said output means respectively, said difference in the number of signals in said first and second series of signals being a function of the gradient of the torque transmitted by the coupling means.

32. The method according to claim 31 in which information representative of the maximum torque gradient developed up to any given point during the driving of said assembly is stored.

33. The method according to claim 30 in which the datum number of consecutive signals in said second series of signals is counted starting only from selected signals in said second series.

34. The method of determining stiffness of an assembly using deflectable coupling means for transmitting power from input means to output means for imparting movement to the assembly, the method consisting of the steps of developing a first series of pulses representative of the displacement of said input means;
developing a second series of pulses representative of the displacement by said coupling means of said output means, and
comparing said first and second series of pulses by counting the difference of the number of pulses in said first and second series during a datum number of consecutive pulses in said second series as power is transmitted by said coupling means from said input means to said output means, said difference being a function of the stiffness of said assembly.

35. The method of tightening an assembly including a fastener by power input means driving fastener engaging means through deflectable coupling means, the method consisting of the steps of developing
a first series of signals representative of the displacement of said power input means;
a second series of signals representative of the displacement by said coupling means of said fastener engaging means;
comparing said first and second series of signals by counting the difference of the number of signals in said first and second series of signals during a datum number of consecutive signals in said second series of signals as power is transmitted by said coupling means from said power input means to said fastener engaging means, said difference being a function of the instantaneous stiffness of the assembly;
sequentially storing information representative of the maximum stiffness of the assembly developed during the tightening of the assembly, and
producing a control signal controlling said power input means when said instantaneous stiffness has dropped to a predetermined ratio of the maximum stiffness developed during the tightening of the assembly.

36. The method of tightening a screw-threaded fastener by rotary power input means driving fastener engaging means through torsionally deflectable coupling means, the method consisting of the steps of developing
a first series of signals representative of the rotary displacement of said rotary power input means;
a second series of signals representative of the displacement by said coupling means of said fastener engaging means;
comparing said first and second series of signals by counting the difference of the number of signals in said first and second series of signals during a datum number of consecutive signals in said second series of signals as power is transmitted by said coupling means from said rotary power input means to said fastener engaging means, said difference being a function of the instantaneous torque gradient of the fastener;

sequentially storing information representative of the maximum torque gradient developed during the tightening of the fastener, and producing a control signal controlling said rotary power input means when said instantaneous torque gradient has dropped to a predetermined ratio of the maximum torque gradient developed during the tightening of the fastener.

37. The method according to claim 36 in which said control signal is produced when said instantaneous torque gradient has dropped to substantially 50% of the maximum torque gradient developed during the tightening of the fastener.

38. The method according to claim 36 in which said control signal is employed to stop said power input means.

39. The method according to claim 36, in which said control signal is produced when said instantaneous torque gradient has dropped to between approximately 25% to 75% of the maximum torque gradient developed during the tightening of the fastener.

40. Apparatus for tightening an assembly including a threaded fastener comprising:

first means for imparting torque and rotation to said fastener;

second means connected to said first means for developing a signal representative of the instantaneous gradient of the torque-rotation curve through which the assembly is being tightened; and third means responsive to said gradient signal for determining a significant change in slope following a tightening region on the torque-rotation curve through which the assembly is being tightened, said third means including means for storing a signal representative of the gradient of the torque-rotation curve throughout the tightening region thereof and for developing a control signal when said instantaneous gradient signal is a predetermined percentage of said stored signal.

41. Apparatus for tightening a threaded fastener assembly in accordance with claim 40 wherein said stored signal is representative of the maximum gradient of said torque-rotation curve.

42. Apparatus for tightening an assembly including a fastener until the yield point or a similarly significant change in slope of a torque-rotation curve for the assembly has been reached, said apparatus comprising:

wrenching means for imparting torque and rotation to said fastener assembly;

means for developing a signal representative of the instantaneous torque imparted to said fastener assembly;

means for developing a signal representative of the angular rotation of said fastener assembly;

means responsive to said torque signal and said rotation signal for developing a signal representative of the instantaneous torque gradient of the torque-rotation curve through which said fastener assembly is being tightened;

means responsive to one of said signals having a certain relationship relative to said torque gradient signal through the tightening region of said torque-rotation curve for developing a control signal.

43. Apparatus for tightening a fastener assembly in accordance with claim 42 wherein said one of said signals is the torque gradient signal.

44. Apparatus for tightening a fastener assembly in accordance with claim 42 wherein said means for developing said torque gradient signal includes means for determining the largest torque gradient signal developed up to any point and wherein said means for developing said control signal includes means for comparing said largest torque gradient signal and said instantaneous torque gradient signal.

45. Apparatus for tightening a fastener assembly in accordance with claim 44 wherein said control signal is developed when said instantaneous torque gradient signal is a predetermined percentage of said largest torque gradient signal.

46. Apparatus for tightening a fastener assembly in accordance with claim 45 wherein said predetermined percentage is any percentage substantially 50% or less.

47. Apparatus for tightening a fastener in accordance with claim 45 wherein said predetermined percentage is between approximately 25% to 75%.

48. Apparatus for tightening a fastener assembly in accordance with claim 44 wherein said means for determining the largest gradient signal developed up to any point includes storage means for storing the largest gradient signal so far developed and comparator means for comparing said stored gradient signal with said instantaneous gradient signal and providing an output signal when said instantaneous gradient signal is larger than said stored gradient signal, said comparator means output signal being said larger instantaneous gradient signal and said storage means receiving said comparator means output signal.

49. Apparatus for tightening a fastener assembly in accordance with claim 42 wherein said means for developing said torque signal comprises torque cell means.

50. Apparatus for tightening a fastener assembly in accordance with claim 49 wherein said torque cell means includes a member twisting about its axis and being associated with strain gauge means.

51. Apparatus for tightening a fastener assembly in accordance with claim 49 wherein said torque cell means is responsive to the reaction torque on said wrenching means.

52. Apparatus for tightening a fastener assembly in accordance with claim 49 wherein said means for developing said rotation signal includes proximity detector means.

53. Apparatus for tightening a fastener assembly in accordance with claim 52 wherein said proximity detector means is mounted in said wrenching means adjacent a plurality of rotating vanes mounted in a motor supplying power to said wrenching means.

54. Apparatus for tightening a fastener assembly in accordance with claim 42 wherein said means for developing said torque signal includes a deflectable coupling and sensing means at each end of said coupling means for determining the deflection thereof.

55. Apparatus for tightening a fastener assembly in accordance with claim 42 wherein said means for developing said rotation signal includes proximity detector means.

56. Apparatus for tightening a fastener assembly in accordance with claim 55 wherein said proximity detector means is mounted in said wrenching means adjacent a plurality of rotating vanes mounted in a motor supplying power to said wrenching means.

57. Apparatus for tightening a fastener assembly in accordance with claim 42 wherein said means for developing said torque gradient signal incudes a series of sample and hold circuit means.

58. Apparatus for tightening a fastener assembly in accordance with claim 57 wherein said sample and hold circuit means are clocked sequentially to provide output signals.

59. A meter for determining the yield point or a similarly significant change in the slope of any torque-rotation curve comprising:
- means for developing a changing signal representative of the torque gradient of the torque imparted to an assembly;
- means responsive to said gradient signal for storing an information signal representative of the torque gradient developed through the generally linear portion of the torque-rotation curve; and,
- comparator means for comparing said gradient signal and said information signal and developing a control signal when said gradient signal has changed to a predetermined percentage of said information signal.

60. A meter in accordance with claim 59 wherein said information signal is representative of the largest torque gradient developed up to any point.

61. A meter in accordance with claim 59 wherein said comparator means develops said control signal when said gradient signal is substantially 50% or less of said information signal.

62. A meter in accordance with claim 59 wherein said means for developing said gradient signal includes means for generating said gradient signal over a predetermined chord length along the torque-rotation curve at constant intervals whereby said chord lengths overlap.

63. A meter in accordance with claim 59 wherein said means for developing said gradient signal includes means for developing a signal representative of the instantaneous torque imparted to said assembly, storage means for storing a series of signals representative of instantaneous torque and gradient register means for sequentially subtracting one of said stored signals from said instantaneous torque signal.

64. A meter in accordance with claim 63 wherein said storage means is responsive to signals generated at constant increments of rotation of said assembly for sequentially feeding one of said stored signals to said gradient register means.

65. A meter in accordance with claim 63 wherein said storage means comprises shift register means responsive to signals generated by an encoder rotatable with said assembly.

66. A meter in accordance with claim 59 including means for imparting torque and rotation to said assembly.

67. A meter in accordance with claim 66 wherein said torque and rotation imparting means comprises wrenching means and wherein said assembly comprises a threaded fastener.

68. A meter in accordance with claim 59 wherein said means for developing said gradient signal includes analog shift register means.

69. A meter in accordance with claim 68 wherein said analog shift register means includes a series of sample and hold circuit means.

70. A meter in accordance with claim 69 wherein said sample and hold circuit means are clocked sequentially.

71. A meter in accordance with claim 59 wherein said information signal is representative of the largest torque gradient developed up to any point and wherein said means responsive to said gradient signal includes storage means for storing the largest gradient signal and comparator means for comparing a stored gradient signal with an instantaneous gradient signal and providing an output signal when the instantaneous gradient signal is larger than the stored gradient signal, said comparator output signal being operative to feed said instantaneous gradient signal to said storage means.

72. A meter in accordance with claim 59 wherein said comparator means develops said control signal when said gradient signal is between approximately 25% to 75% of said information signal.

73. A method of tightening an assembly including a fastener by power input means driving a fastener engaging means, the method comprising:
- applying torque and rotation to the fastener;
- developing a changing signal representative of the torque gradient of the torque imparted to the fastener with respect to the rotation thereof;
- determining the largest torque gradient developed up to any point and storing an information signal representative thereof; and,
- comparing said stored information signal and said gradient signal and developing a control signal when said gradient signal has changed to a predetermined percentage of said information signal.

74. A method in accordance with claim 73 wherein said control signal is developed when said gradient signal has dropped to substantially 50% or less of said information signal.

75. A method in accordance with claim 73 wherein said gradient signal is developed by determining the torque imparted to said fastener and determining the change in torque at constant intervals of angular rotation of said fastener.

76. A method in accordance with claim 73 wherein said control signal is developed when said gradient signal has dropped to between approximately 25% to 75% of said information signal.

77. Apparatus for determining torque gradient comprising means for developing a signal representative of the instantaneous torque applied to a rotary member, storage means for storing a series of signals representative of instantaneous torque and gradient register means for sequentially subtracting a stored signal from an instantaneous torque signal and developing a signal representative of the torque gradient.

78. Apparatus for determining torque gradient in accordance with claim 77 wherein said storage means is responsive to signals generated at constant increments of rotation of said rotary member for sequentially feeding one of said stored signals to said gradient register means.

79. Apparatus for determining torque gradient in accordance with claim 78 wherein said storage means comprises shift register means responsive to signals generated by a pulse generator rotatable with said rotary member.

80. Apparatus for determining torque gradient in accordance with claim 77 wherein said storage means comprises a series of sample and hold means.

81. Apparatus for determining torque gradient in accordance with claim 80 wherein said sample and hold means are clocked sequentially.

82. A method of determining the yield point or a similarly significant change in slope of any torque-rotation curve comprising:
- applying torque and rotation to a member;
- developing a changing signal representative of the torque gradient of the curve which could be plotted for the torque imparted to the member with respect to the rotation thereof;
- determining the torque-gradient in the generally linear portion of said curve and storing an information signal representative thereof; and,
- comparing said stored information signal and said gradient signal and developing a control signal when said gradient signal has changed to a predetermined percentage of said information signal.

83. Apparatus for sensing a desired point on a curve representing the variation of two related inputs, generated by an external source, wherein said related inputs are torque and rotation imparted to a threaded fastener, said curve is the torque-rotation curve through which the fastener is being tightened, and wherein said curve has a generally linear portion and said desired point lies beyond said generally linear portion, said apparatus comprising:
- first means for developing a signal representative of the instantaneous gradient of said curve, and
- second means responsive to said gradient signal for determining a significant change in slope of said curve containing said desired point, said second means including means for storing a signal representative of the gradient of said curve in the generally linear portion thereof and for developing a control signal when said instantaneous gradient signal in the portion of said curve beyond said generally linear portion has a predetermined relationship relative to said stored signal.

84. Apparatus in accordance with claim 83 wherein said stored signal is representative of the maximum gradient of said curve.

85. Apparatus for sensing a significant change in slope beyond a generally linear portion on a curve representing the variation of first and second related variables, wherein said related variables are torque and rotation imparted to a threaded fastener and said curve is the torque-rotation curve through which the fastener is being tightened, said apparatus comprising:
- first means for continuously measuring the torque applied to the fastener;
- second means for comparing different measurements of torque at discrete intervals of rotation of the fastener to develop instantaneous difference signals representative of the instantaneous gradient of said curve;
- third means for comparing instantaneous difference signals with the largest difference signal previously developed and for storing the largest difference signal so far developed representative of the largest instantaneous gradient so far encountered on said curve; and
- fourth means responsive to said instantaneous difference signals and said stored difference signal for developing a control signal when said instantaneous difference signal has a predetermined relationship relative to said stored difference signal.

86. Apparatus in accordance with claim 85 wherein said second means compares an instantaneous measurement of torque with a measurement of torque a plurality of discrete intervals previouus to said instantaneous measurement.

87. Apparatus in accordance with claim 85 wherein said fourth means develops a signal representative of a predetermined percentage of the largest stored maximum gradient signal, and wherein said predetermined percentage signal is compared to said instantaneous gradient signal and said control signal is produced when the compared signals are approximately equal.

88. Apparatus in accordance with claim 87 wherein said predetermined relationship is a percentage between approximately 25% to 75%.

89. Apparatus for tightening an assembly including a threaded fastener, said apparatus comprising:
- first means for imparting torque and rotation to said fastener;
- second means connected to said first means for developing a signal representative of the instantaneous gradient of the torque-rotation curve through which the assembly is being tightened; and
- third means responsive to said gradient signal for determining a significant change in slope on the torque-rotation curve through which the assembly is being tightened, said third means including means for storing a signal representative of the maximum gradient of the torque-rotation curve throughout the tightening region thereof and for developing a control signal when said instantaneous gradient signal is a predetermined percentage of said stored signal.

* * * * *

UNITED STATES PATENT AND TRADEMARK OFFICE
CERTIFICATE OF CORRECTION

PATENT NO. : 3,982,419
DATED : September 28, 1976
INVENTOR(S) : John T. Boys

It is certified that error appears in the above—identified patent and that said Letters Patent are hereby corrected as shown below:

Column 6, line 56, " $\frac{\Delta M}{\Delta \phi_2} =$ " has been omitted; the equation should read $-- \frac{\Delta M}{\Delta \phi_2} = K \frac{\Delta \phi_1 - \Delta \phi_2}{\Delta \phi_2} --$;

Column 7, line 14, "be" should read -- by --;
Column 7, line 60, "is" (first occurrence) should read -- as --;
Column 8, line 12, "Acordingly" should read -- Accordingly --;
Column 9, lines 42 and 44, "stop" should be in quotes in each line and should read -- "stop" --;
Column 10, line 64, "rgisters" should read -- registers --;
Column 10, line 65, the comma "," should be a period -- . --;
Column 10, line 66, "register 1" should read -- registers '1' --;
Column 10, line 68, "0" should read -- '0' --;
Column 11, line 45, "noise" should be in quotes and should read -- "noise" --;
Column 12, line 11, "the" (first occurrence) should read -- that --;
Column 12, line 33, "of" should be deleted;
Column 12, line 36, "and" should be deleted;
Column 12, line 45, "twised" should read -- twisted --;
Column 16, line 57, "the" should be deleted;
Claim 10, line 1, "4" should read -- 8 --;
Claim 30, line 1, "if on" should read -- of an --;
Claim 86, line 4, "previouus" should read -- previous --.

Signed and Sealed this

Twenty-second Day of March 1977

[SEAL]

Attest:

RUTH C. MASON
Attesting Officer

C. MARSHALL DANN
Commissioner of Patents and Trademarks

REEXAMINATION CERTIFICATE (144th)

United States Patent [19]

Boys

[11] B1 3,982,419

[45] Certificate Issued Dec. 6, 1983

[54] APPARATUS FOR AND METHOD OF DETERMINING ROTATIONAL AND LINEAR STIFFNESS

[75] Inventor: John T. Boys, Christ Church, New Zealand

[73] Assignee: Standard Pressed Steel Co., Jenkintown, Pa.

Reexamination Request:
No. 90/000,256, Sep. 13, 1982

Reexamination Certificate for:
Patent No.: 3,982,419
Issued: Sep. 28, 1976
Appl. No.: 507,417
Filed: Sep. 19, 1974

Related U.S. Application Data

[63] Continuation-in-part of Ser. No. 357,920, May 7, 1983, abandoned.

[30] Foreign Application Priority Data

May 9, 1972 [GB] United Kingdom ............ 21480/72

[51] Int. Cl.³ .................... B25B 23/14; B23P 19/06; G01D 1/10; G01D 1/16
[52] U.S. Cl. .................................. 73/862.24; 73/761; 73/764; 73/772; 73/774; 73/789; 73/847; 73/862.34; 173/12
[58] Field of Search ............ 73/761, 789, 847, 862.23, 73/862.24, 770, 772, 791, 805, 814; 364/508, 552, 828

[56] References Cited

U.S. PATENT DOCUMENTS

| | | | |
|---|---|---|---|
| 2,600,549 | 6/1952 | Ledbetter | 73/862.23 X |
| 2,912,861 | 11/1959 | Coyne et al. | 73/DIG. 1 |
| 3,076,603 | 2/1963 | Gruber | 73/772 X |
| 3,316,394 | 4/1967 | Fluhr | 364/828 |
| 3,424,987 | 1/1969 | Fluhr | 364/828 X |
| 3,477,286 | 11/1969 | Baker | 73/770 |
| 3,554,019 | 1/1971 | van den Hove et al. | 73/772 |
| 3,558,866 | 1/1971 | Poulson | 73/772 X |
| 3,643,501 | 2/1972 | Pauley | 73/862.24 |
| 3,661,012 | 5/1972 | Yamazaki et al. | 73/791 |
| 3,693,726 | 9/1972 | Hornig et al. | 73/862.24 X |
| 3,733,049 | 5/1973 | van den Hove et al. | 73/772 X |
| 3,916,673 | 11/1975 | Gass et al. | 73/37 |
| 4,013,895 | 3/1977 | Akiyoshi et al. | 73/862.23 X |

OTHER PUBLICATIONS

J. B. Johnson, "The Materials of Construction", pub. by John Wiley & Sons, pp. 16-21, 1912.
F. B. Seely, "Resistance of Materials", pub. by John Wiley & Sons, pp. 16-25, 1948.
A. D. Merriman, "A Concise Encyclopedia of Metallurgy", pub. by McDonald & Evans, Ltd., p. 432, 1965.

*Primary Examiner*—Charles A. Ruehl

[57] ABSTRACT

A meter for determining stiffness or torque gradient including, in one embodiment, a deflectable coupling connected between an output shaft and a power input shaft, sensing means for developing two separate series of signals representative of the displacement of the input and output shafts respectively, a comparator for determining from the two series of signals a function of the stiffness or torque gradient and, in another embodiment, including a single shaft having an input end and an output end, transducer means associated with the shaft for developing a signal representative of the torque being applied through the shaft, sensing means for developing a signal representative of the displacement of the shaft, and comparator means for determining from the two signals a function of the stiffness or torque gradient. Either embodiment of the stiffness meter may be used for tightening a fastener by including an additional circuit responsive to the comparator output for sequentially storing information representative of the maximum stiffness developed up to any given point during the tightening operation and for producing a stop signal when the instantaneous stiffness has dropped to a predetermined ratio of the maximum stiffness.

REEXAMINATION CERTIFICATE ISSUED UNDER 35 U.S.C. 307.

APPARATUS FOR AND METHOD OF DETERMINING ROTATIONAL AND LINEAR STIFFNESS

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-39, 42-82, and 85-88 is confirmed.

Claims 40, 83, and 89 are determined to be patentable as amended:

Claims 41 and 84, dependent on amended claims, are determined to be patentable.

40. Apparatus for tightening an assembly including a threaded fastener comprising:
   first means for imparting torque and rotation to said fastener;
   second means connected to said first means for developing a signal representative of the instantaneous gradient of the torque-rotation curve through which the assembly is being tightened; and
   third means responsive to said gradient signal for determining a significant change in slope following a tightening region on the torque-rotation curve through which the assembly is being tightened, said third means including means for storing [a] *said* signal representative of the gradient of the torque-rotation curve throughout the tightening region thereof and for developing a control signal when said instantaneous gradient signal is a predetermined percentage of said stored signal.

83. Apparatus for sensing a desired point on a curve representing the variation of two related inputs, generated by an external source, wherein said related inputs are torque and rotation imparted to a threaded fastener, said curve is the torque-rotation curve through which the fastener is being tightened, and wherein said curve has a generally linear portion and said desired point lies beyond said generally linear portion, said apparatus comprising:
   first means for developing a signal representative of the instantaneous gradient of said curve, and
   second means responsive to said gradient signal for determining a significant change in slope of said curve containing said desired point, said second means including means for storing [a] *said* signal representative of the gradient of said curve in the generally linear portion thereof and for developing a control signal when said instantaneous gradient signal in the portion of said curve beyond said generally linear portion has a predetermined relationship relative to said stored signal.

89. Apparatus for tightening an assembly including a threaded fastener, said apparatus comprising:
   first means for imparting torque and rotation to said fastener;
   second means connected to said first means for developing a signal representative of the instantaneous gradient of the torque-rotation curve through which the assembly is being tightened; and
   third means responsive to said gradient signal for determining a significant change in slope on the torque-rotation curve through which the assembly is being tightened, said third means including means for storing [a] *said* signal representative of the maximum gradient of the torque-rotation curve throughout the tightening region thereof and for developing a control signal when said instantaneous gradient signal is a predetermined percentage of said stored signal.

* * * * *